United States Patent [19]

Brennan et al.

[11] Patent Number: 4,587,793

[45] Date of Patent: May 13, 1986

[54] PHARMACEUTICAL INFUSION PRODUCTS AND THE PROCESS AND APPARATUS FOR THE MAKING THEREOF

[75] Inventors: Eric L. Brennan; Kenneth W. Schawel, both of Mission Viejo, Calif.

[73] Assignee: Home Health Care of America, Inc., Newport Beach, Calif.

[21] Appl. No.: 692,653

[22] Filed: Jan. 16, 1985

[51] Int. Cl.$^4$ .......................................... B65B 55/02
[52] U.S. Cl. .................................. 53/425; 53/111 R; 53/428; 53/434
[58] Field of Search ............ 53/425, 426, 428, 111 R, 53/512, 510, 434, 432; 141/95, 96, 85, 93; 210/764, 636, 645, 90, 137, 741, 765; 366/162

[56] References Cited

U.S. PATENT DOCUMENTS

| | | | |
|---|---|---|---|
| 3,035,886 | 5/1962 | Hickey | 53/425 X |
| 3,815,315 | 6/1974 | Glick | 53/425 |
| 4,332,122 | 6/1982 | Williams | 53/425 |
| 4,372,100 | 2/1983 | Miller et al. | 53/428 |
| 4,522,015 | 6/1985 | Hildebolt | 53/425 |

*Primary Examiner*—James F. Coan
*Attorney, Agent, or Firm*—George F. Bethel; Patience K. Bethel

[57] ABSTRACT

A novel aseptic process for the preparation of intravenous and other pharmaceutical products, especially parenteral solution is provided as well as the pharmaceutical products produced thereby. The process involves ambient temperature mixing, filtering and filling in special enclosures, the surfaces of which have been rendered free of pathogenic organisms. The enclosures are further provided with sterile air by filtration through high efficiency particulate air filters. Positive pressure sterile air is caused to flow across the enclosure in a unidirectional, substantially lateral flow pattern in a generally diagonal direction, to effect a sweeping of sterile air in a continuous manner through the enclosure. Compounding of ingredients preferably is conducted in a separate enclosure from the filtration and filling processes. The apparatus is free of pathogenic organisms and includes a novel backflow pressure manifold system to control internal pressure exerted in the filtering and filling tubing. The novel products produced by the invention process can be stored for extended periods at refrigeration temperatures allowing infusion to be made available on a home care basis. New parenteral solutions are also provided which are compounded from the bulk powders of amino acids, dextrose, and electrolytes.

28 Claims, 7 Drawing Figures

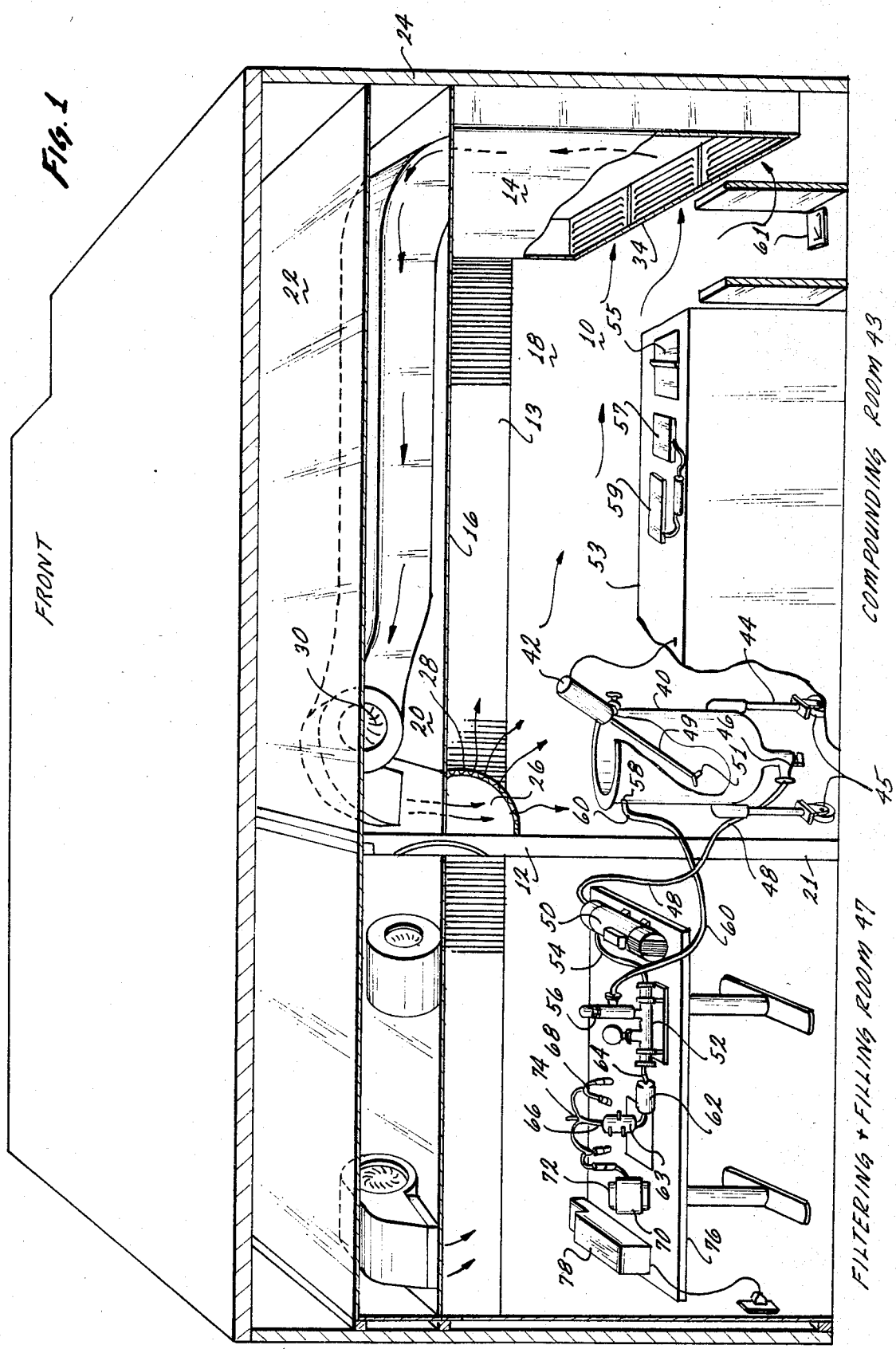

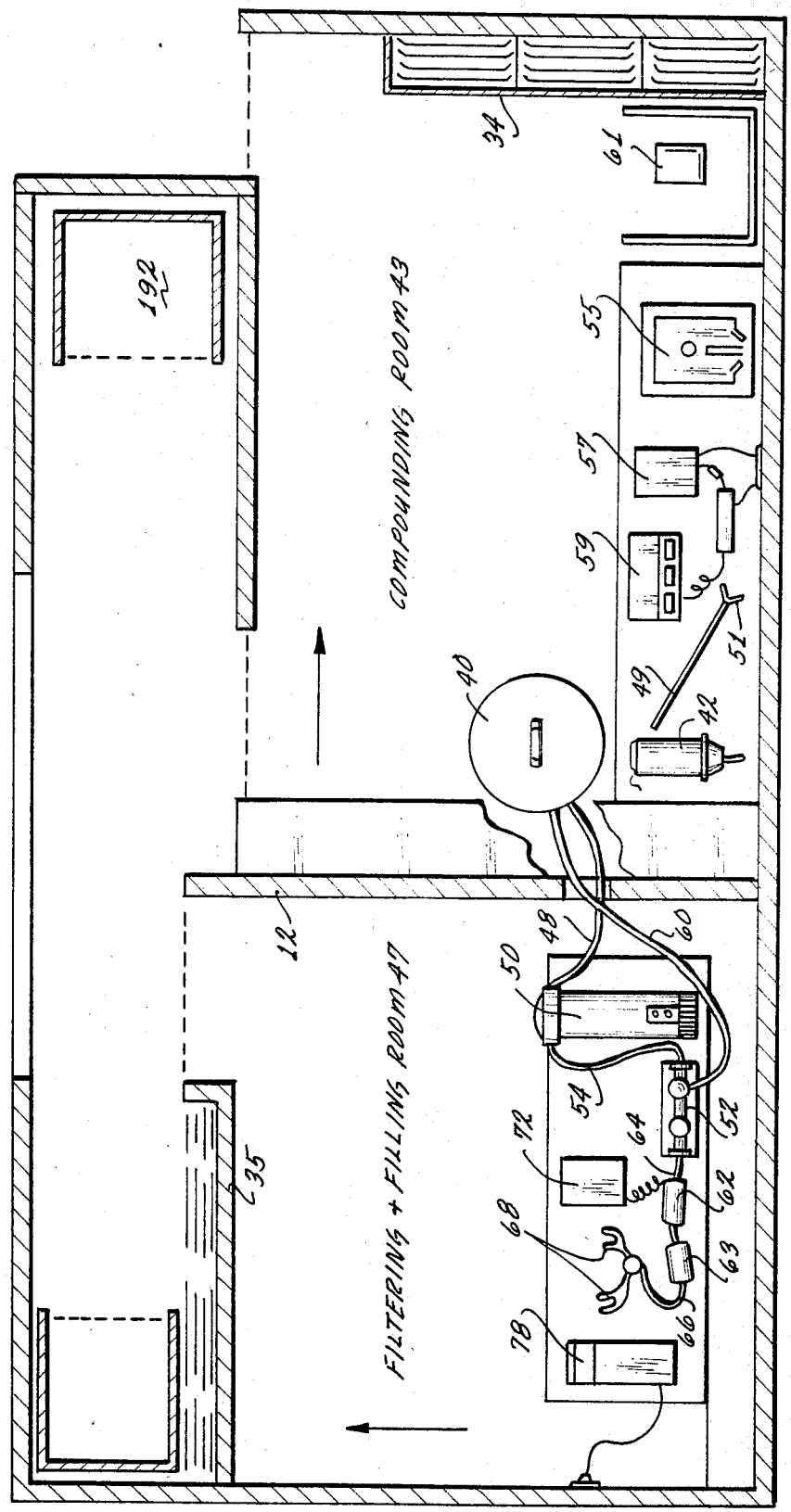

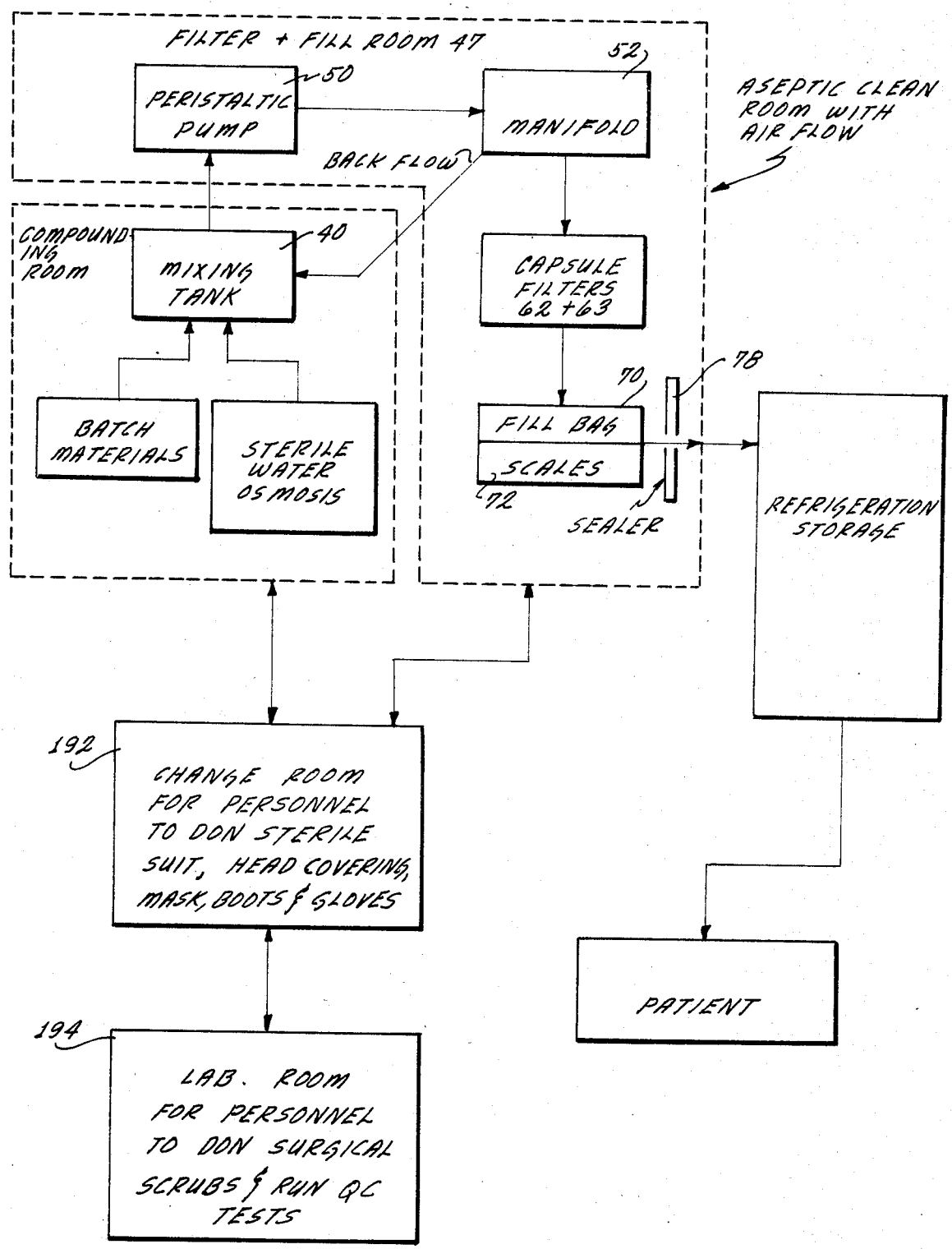

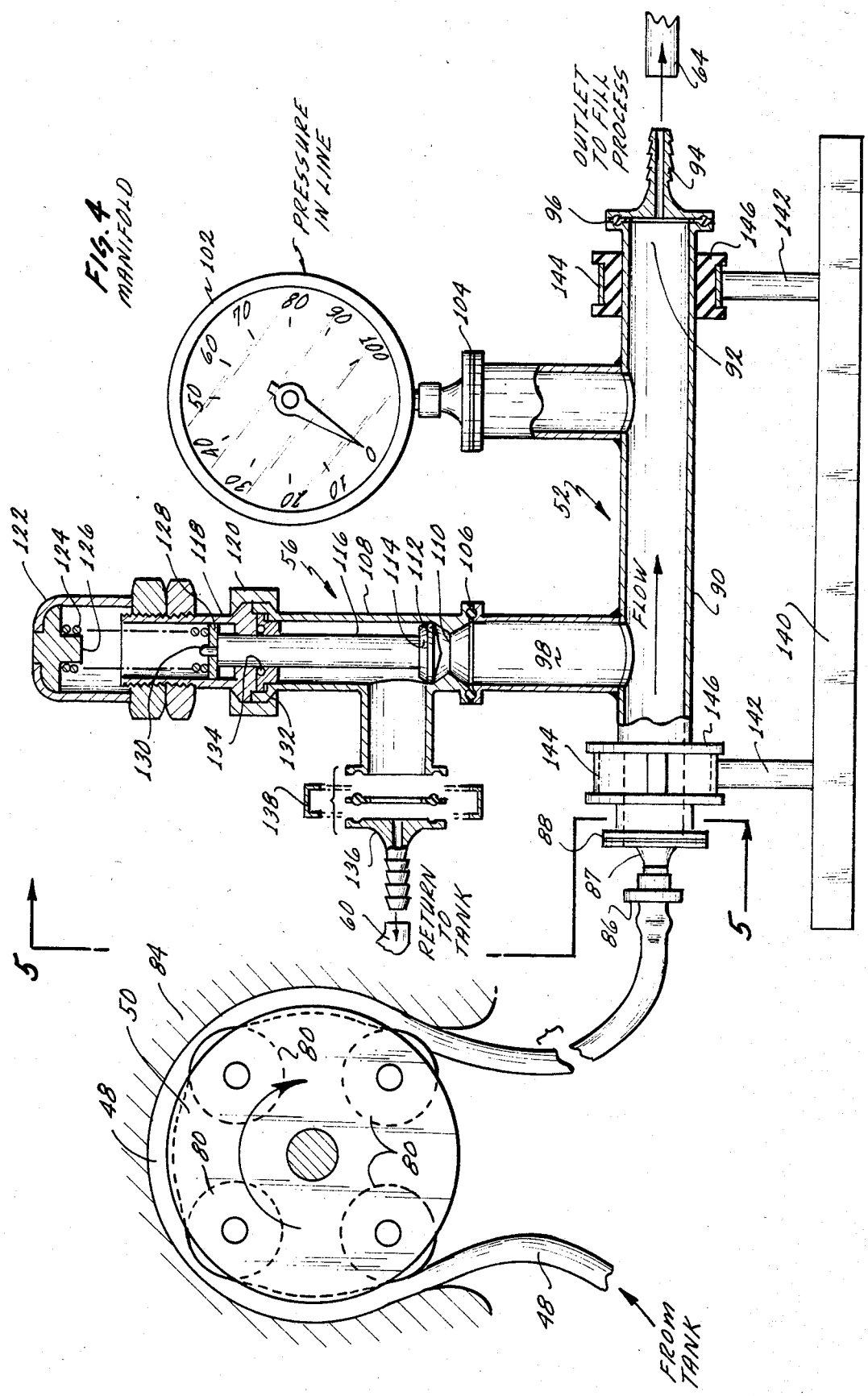

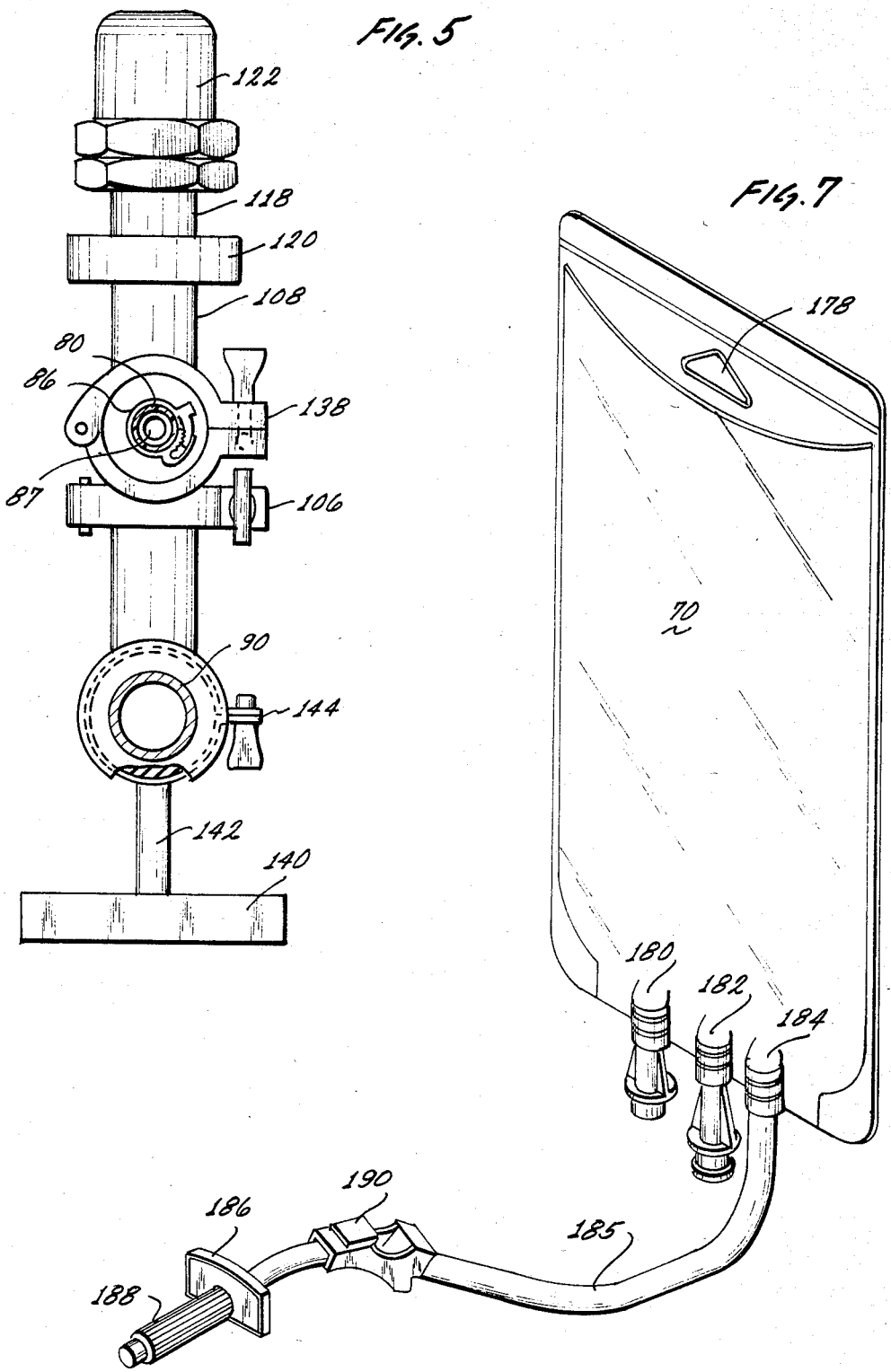

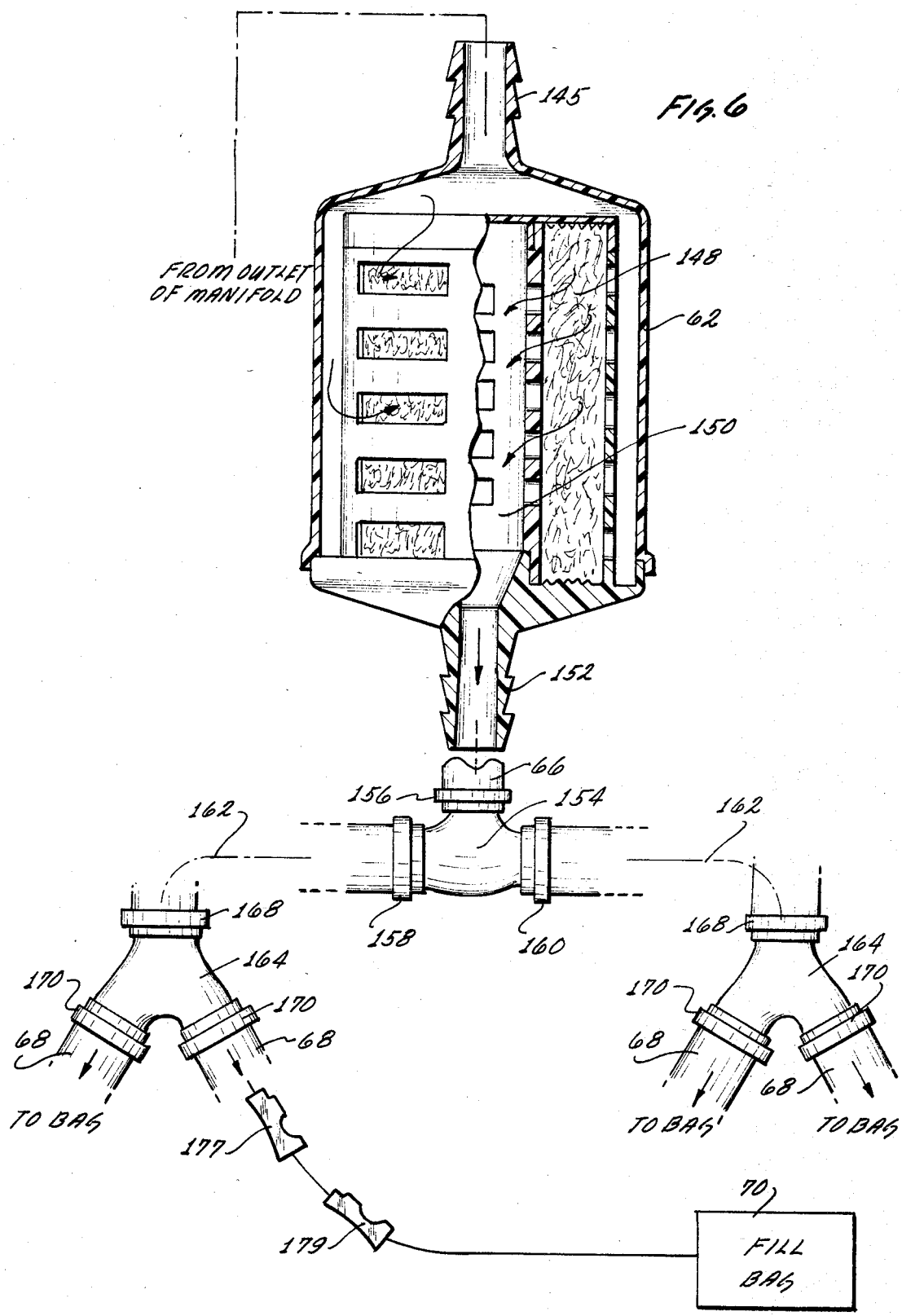

PHARMACEUTICAL INFUSION PRODUCTS AND THE PROCESS AND APPARATUS FOR THE MAKING THEREOF

FIELD OF THE INVENTION

This invention relates to the field of the pharmaceutical arts. More specifically, it resides within the compounding and packaging of liquid pharmaceutical products under aseptic conditions for infusion purposes particularly of total parenteral nutrition, and to the products produced thereby. Liquid pharmaceutical prescription products for the intravenous feeding of essential nutrients directly into the bloodstream (parenteral nutrition) are provided.

In addition, the invention is directed toward the aseptic preparation of relatively large scale batches of liquid prescription infusion products for parenteral nutrition, as well as to the aseptic preparation of other intravenous solutions utilizing a novel filtering apparatus.

BACKGROUND OF THE INVENTION

Total parenteral nutrition can be defined as the feeding of nutrients by means of infusion into the bloodstream of patients who are unable to digest food properly as a result of disease, surgery, or in the case of premature infants, premature development thereof.

For example, total parenteral nutrition has been successfully employed with patients having gastrointestinal disorders, such as ulcerative colitis, Crohn's disease, ischemic bowel infarction, short bowel syndrome, malabsorption due to radiation enteritis, intestinal fistulas, cancers of the gastrointestinal tract, severe dumping syndrome, and total gastrectomy.

Premature infants have also benefited by total parenteral nutrition, as well as infants having chronic diarrhea or congenital gastrointestinal anomalies.

Home care using infusion such as total parenteral nutrition has been successfully employed in the treatment of pediatric patients having serious conditions such as AIDS, acidemia, dumping syndrome, Batten-Mayou disease, those recovering from bone marrow transplants, Crohn's disease, Fanconi's syndrome, glycogen storage disease, cellulitis, facial rhabdomyosarcoma, Ewing's sarcoma, cerebral palsy, seizure disorder, cystic fibrosis, acute myelocytic and lympo-cytic leukemia, Stevens Johnson syndrome, systemic lupus, erythematosus, tyrosinuria, hemolytic uremic syndrome, and many other disorders.

In the above mentioned conditions, total parenteral nutrition (TPN) has been successfully employed over long term periods. It has been employed for as long as ten or more years, as well as for shorter temporary periods, during which time the initial underlying condition is given a chance to heal itself.

Patients suffering from the above bowel disorders exhibit general malnutrition with the consequent loss of weight, muscular weakness, poor wound healing, reduced immunocompetence, and general impeded recovery from primary illnesses.

As a general requirement, the body must be supplied daily with adequate amounts of carbohydrates, proteins, fats, vitamins, minerals and water. The actual makeup of the TPN liquid is individually established for each patient and is produced to conform to a doctor's prescription. A typical composition of TPN liquid includes dextrose or glucose, amino acids, and electrolytes in the form of various minerals and water. Vitamins, other minerals, fatty acids, and medicines, are generally not compounded with the above materials but are rather combined just prior to infusion with the TPN solution.

Infusion of the TPN solution within the body takes place by means of a catheter which has been implaced within a large vein close to the heart. The catheter insertion is made under a local anesthetic into the anterior upper abdominal wall and tunneled subcutaneously to the target vein, which can be a cephalic, subclavian, pectoral, thyrocervical common facial, internal jugular or external jugular vein, and thence to the superior vena cava.

The use of the central vein is necessary to prevent thrombosis or clotting, which would occur if a smaller peripheral vein in the hand or arm were used.

The other end of the catheter is tunneled under the skin and exits in the middle of the chest. It incorporates a dacron velour cuff that lies under the skin in order to allow the body tissue to grow into the cuff and anchor the catheter.

Once the catheter is implaced and covered with a cap known as a luer-lok, the patient is then ready to receive parenteral nutrition or intravenous hyperalimentation, which is used interchangeably in this specification.

The foregoing described feeding of parenteral solutions has been used in hospitals since about 1966 and has been successfully adapted in recent years for use at home.

Most commonly, the TPN solution is contained within the sterile clear plastic bag or other container such as a bottle. A tube from the TPN container is provided with a luer-lok connection.

The preferred method of infusion is to connect the tube from the container of TPN liquid to the patient's catheter by means of the luer-lok connection. Control of the flow of the solution throughout the prescribed number of hours is provided by means of an electronic infusion pump or positive pressure pump. Ideally, the infusion takes place during sleep so that the patient is not inconvenienced during the day and can resume normal activities.

It can be appreciated that since the TPN liquid is directly infused into the bloodstream that it is of paramount importance not to introduce any organisms into the body through the TPN solution.

It is to the aseptic compounding of pharmaceutical liquids, especially parenteral liquids, that this invention is directed, as well as to the process for their preparation and the apparatus which is used in conjunction therewith.

In the past, parenteral solutions were prepared separately on an individual patient prescription basis just prior to each infusion. Typically, heat sterilized dextrose solutions and heat sterilized amino acid solutions were mixed together under a laminar flow hood according to one of two methods.

According to the first method, all of the additions except the calcium gluconate and magnesium sulfate are added to and mixed with the heat sterilized amino acid solution. The calcium and magnesium components are then added to and mixed with the heat sterilized dextrose solution, followed by mixing together of the two resulting solutions.

The second individual patient prescription procedure involves mixing together the heat sterilized dextrose and heat sterilized amino acid solutions followed by the additions of the other materials and finally, the calcium and magnesium compounds.

The above procedures are known as unit mix procedures, since they are used for only one infusion of a patient. They generally are infused within one hour sometimes utilizing an inline filter of 0.22 microns.

Since unit mix solutions are made up on an individual patient basis requiring from five to fifteen manipulative steps, the opportunity for introduction of pathogenic organisms is high. However, since each unit mix solution is generally infused into a patient within about one hour from preparation, there is little danger of growth of pathogens.

By contrast, the invention and process of this application uses one connection from the mixing tank to the fill bag in which all of the solution is filtered under aseptic conditions. This minimizes the opportunity for contamination by pathogens.

The significance of the present invention is to provide uniformity of nutrition to a specific patient, since as much as a month's supply can be produced according to the process of the invention in one batch mixing. This permits the patient to rely not only on the uniformity of the TPN liquid, but also to rely on the absence of pathogens within the TPN solution. Furthermore, the process permits the manufacture of the TPN liquids at greatly reduced cost over hospital techniques by as much as sixty percent less. The reduced cost, as well as the consistency, enable many patients to be parenterally infused at home. This permits them to lead a normal life as much as possible.

The process provided by this invention specifies very specific working conditions. Non-pathogenic positive flow sterile air is caused to flow over the work surfaces and apparatus which have been treated to remove pathogenic organisms. The interior surfaces of the clean room are similarly treated. In addition, the aseptic techniques, utilizing a filtering apparatus which has also been rendered free of pathogenic organisms, coupled with a single connection from the mixing tank to the fill bag permits the cold sterilization of the TPN solutions.

By this means, novel TPN solutions can be made, if desired, from the powdered amino acids and powdered dextrose directly. Furthermore, individual amino acid profiles can be adjusted as required. In pediatric use this can be required quite often.

The TPN solutions produced hereby are capable of extended storage by as long as thirty to sixty days under refrigeration. By contrast, unit mixed solutions with their opportunities for the introduction of pathogenic organisms are probably of questionable safety after about fourteen days.

SUMMARY OF THE INVENTION

This invention sets forth a pharmaceutical process and apparatus for the aseptic compounding of liquid pharmaceutical products. It includes a specific filtering apparatus for use therein, and the liquid pharmaceutical products produced thereby. The process and apparatus are specifically suited for the production of parenteral nutrition products, as well as other intravenous or infusion solutions.

The process includes compounding the liquid pharmaceutical products in a clean room enclosure, in which the walls, ceiling, floors, work surfaces and equipment are substantially free of pathogenic organisms. Positive pressure air is provided which is caused to flow through a high efficiency particulate air filter. Preferably, the air is made to flow in a unidirectional, substantially lateral flow pattern diagonally across the clean room. A portion of the air is refiltered and recirculated with prefiltered makeup air.

The apparatus which is used for the aseptic compounding of the liquid pharmaceutical products includes a mixing tank which is equipped with a stirring means in which the ingredients of the pharmaceutical mixture are added, and mixed. The mixing tank is located in a clean room or enclosure which is separate from the clean room in which the filtering and filling apparatus is located. Tubing from the mixing tank is passed through an opening in the wall of its enclosure to the clean room or enclosure containing the filtering and filling apparatus.

The mixing tank has an outlet near its bottom which communicates with a manifold by means of tubing. A peristaltic pump provides positive displacement by contact with tubing which interconnects the tank and manifold.

The manifold is provided with a back pressure valve which permits return of at least a portion of the liquid pharmaceutical product to the tank when a predetermined internal pressure is reached. A pressure gauge responsive to adjustment of the back pressure valve permits the selection of the minimum pressure which will cause the back pressure valve to open.

Downstream from the manifold are two liquid filters. A pre-filter precedes a high efficiency filter which has pores small enough to preclude flow of pathogenic organisms therethrough. The high efficiency filter (0.22 micron), in turn, connects with a fill tube and a fill bag, or container for the product. When each bag has been filled, it is hermetically sealed and another takes its place.

According to a preferred embodiment, crystalline powdered ingredients, i.e., dextrose, amino acids, and electrolytes included in a prescription parenteral liquid, can be directly mixed and filtered according to the process. This provides an additional advantage in that the amino acid profile can be individually adjusted to each patient's needs. This is especially important for pediatric patients. The resulting products are sterile and can be stored under refrigeration for extended periods of time.

DESCRIPTION OF THE DRAWINGS

The invention will be more readily understood by reference to the description which follows taken with the drawings in which:

FIG. 1 shows a perspective view of the apparatus and facilities of the invention;

FIG. 2 shows a schematic plan view of the apparatus and facilities of the invention;

FIG. 3 shows a block flow diagram of the invention process;

FIG. 4 shows an enlarged partially sectioned and somewhat schematic view of the pressure regulating manifold of the invention in conjunction with a peristaltic pump;

FIG. 5 is a side view of the pressure regulating manifold as viewed from the direction of lines 4—4 in FIG. 3;

FIG. 6 shows a partially schematic section of the capsule filter taken in the direction of lines 5—5 of FIG. 1; and, FIG. 7 shows an enlarged detail of the fill bag.

DETAILED DESCRIPTION OF THE INVENTION

Referring now to FIG. 1, there is shown two enclosures or clean rooms 43 and 47. The enclosure 43 includes four walls of which only 12, 13 and 14 are shown, as well as ceiling 16 and floor 18. Surrounding the walls 12 and 14, as well as ceiling 16, is an outer surrounding wall and ceiling combination which forms a plenum 20. Thus, outer wall 21 is spaced from wall 12, outer ceiling 22 is spaced from ceiling 16, and outer wall 24 is spaced from a wall which is shown removed for clarity. The walls can be formed of rigid materials or from flexible plastic films, such as polyethylene chloride films. Openings into the rooms are preferably in the form of overlapping plastic strips extending from the ceiling to provide a sort of louver within the opening. This design permits entry into the clean room with a minimum of air loss. Positive pressure within the clean room prevents introduction of unfiltered outside air.

At the left upper corner of the enclosure 43 is a high efficiency particulate air filter (HEPA) 26 which extends across the width of the wall 12. The filter 26 has a curved configuration and is covered with a curved filter protective screen 28.

A blower 30 within the plenum 20 draws prefiltered air from a source not shown which opens into the plenum 20 and is drawn into the HEPA filter 26 and screen 28. The bulk of the air issuing from the filter 26 is dispersed in a uniform, non-turbulent generally diagonal direction as indicated in FIG. 1 to a low level, louvered air exhaust grill 34 located diagonally opposite the filter 26, which is parallel to and spaced from floor 18 and perpendicular to back wall 24.

The grill 34 extends substantially across the full width of back wall 24 and contains prefilters within it, which are not shown. The air exiting the enclosure 43 through the grill 34 is drawn into the plenum 20 between a front wall, not shown, and back wall 24 and between ceiling 16 and outer ceiling 22. A portion of the air escapes from the clean room or enclosure through the openings for entry. The remaining air together with prefiltered makeup air from a source not shown is recirculated by refiltration through filter 26 and circulated again through the enclosure 43. This continuous action maintains positive pressure througout the room and system.

The filtering system described in detail for compounding room or enclosure 43 is exactly the same as for filtering and filling room 47 even though the detail is not shown. As indicated in FIG. 2, the flow of air in enclosure 43 is at a right angle to the flow of air in enclosure 47. Thus, in enclosure 47 air is drawn into grill 35 in the direction indicated in FIG. 2.

Preferably, the HEPA filter 26 is one providing air filtration efficiency of 99.99% or better for 0.5 micron sized particles. Most preferably, the HEPA filter 26 has the same efficiency for rejection of 0.3 micron sized particles. It has been found that the arrangement of the filter 26 as shown, together with the diagonally opposite return grill 34, provides an extremely efficient sweep of the air issuing from the filter 26 over the work surfaces and other surfaces of the enclosures 43 and 47.

By passage of the air within the enclosures 43 and 47 through the HEPA filter 26 and recirculation through grills 35 and 34 respectively as shown in FIGS. 1 and 2, it is possible to exclude pathogenic organisms and dust particles from contamination within the room. Best results have been obtained when the air within the clean room or enclosure is renewed every fifteen seconds.

The use of non-rigid walls and ceiling permits the possibility of set up for temporary use in virtually any location. Thus, when plastic walls with the plenum 20 are used it permits portability and establishment of facilities without the need for a permanent pharmacy.

It is preferred that the mixing tank 40 be located in a separate clean room or enclosure 43 from the clean room 47 housing the filtering apparatus. The tank 40 can communicate with the filter apparatus by means of tubing 48 and 60 which pass through a common wall of said enclosures 43 and 47.

It is recommended that the mixing tank 40 be located in a separate room, since the chance for contamination is increased if the mixing tank is in the fill room. This is because the materials used in compounding are clean but not sterile.

The compounding and filtering apparatus is shown in FIGS. 1 and 2. The mixing tank 40 as mentioned above is located in a separate clean room or enclosure 43. It is joined to the filtering apparatus through tubing, as explained in detail below.

Compounding room 43 also includes a floor sink 61 with a modular tank wash. A work table 53 includes a sink 55 and a Mettler balance 57 with an Epson computer hook-up 59. The latter are used to accurately measure the pharmaceutical ingredients for each prescription.

A stainless steel mixing tank 40 provided with a mixer 42 having a stainless steel shaft 49 and stainless steel impeller 51 is supported by legs 44 having attached casters 45. An outlet port 46 at the bottom of the tank 40 communicates by means of tubing 48 through walls 12 and 21 of enclosure 43 to a pump 50 on a work table 76 in filtering and filling room 47. The pump 50 communicates with a backflow manifold 52 through tubing 54.

A backflow manifold valve 56 which is located in filtering and filling room 47 communicates with an inlet port 58 of tank 40 by means of tubing 60, which passes through walls 21 and 12 from filtering and filling room 47 to compounding room 43.

As shown in FIGS. 1, 4 and 6, a main flow channel 90 of the manifold 52 communicates with filters 62 and 63 through tubing 64. Tubing 66 from the filter 63 bifurcates to form fill lines 68, one of which is shown attached to a fill bag 70. A stand 74 supports the filter 63 and fill lines 68 during the filtration process.

A fill bag 70 is shown in place on a scale 72 which is used to determine the weight of the product within the fill bag.

Adjacent to the scale 72 on table 76, there is shown a tube sealer 78 which is used to hermetically seal the tubing attached to and integral with the fill bags 70. Sealing the bags keeps the pharmaceutical contents in a sterile condition.

The backflow manifold 52 is shown in greater detail in FIG. 4. Its purpose is to provide controlled flow and to keep the pressure exerted within the tubing within prescribed limits in order to extend the longevity thereof. The longevity of the tubing is primarily a function of the internal pressure exerted within the tube as well as the material of which it is made. By controlling the internal pressure it is possible to maximize the longevity of the tubing within the system.

As shown in FIGS. 1 and 2, tubing 48 from the mixing tank 40 passes through a pump 50. The pump is a peristaltic pump which exerts pressure by means of rollers indicated at 80 in FIG. 4, against flexible tubing 48 supported by a bearing section 84. In this manner, liquid is caused to flow through the flexible tubing 48 without actually coming into direct contact with parts of the pump 50.

The pump 50 causes liquid from within the flexible tubing 48 to enter the manifold 52. The liquid proceeds through a tubing connector 87 onto which the tubing 80 is secured by means of a clamp 86. Connector 87 is secured to the manifold 52 by means of a clamp 88.

As shown, the manifold 52 contains a main flow channel 90 having a main outlet 92 with a tubing connector 94 attached thereto by means of a clamp 96. In addition, there are two secondary outlet ports 98 and 100.

The secondary outlet port 100 is provided with an inline pressure gauge 102 which is constructed of 316 stainless steel. It is attached to the outlet port 100 by means of a clamp 104.

The backpressure valve 56 communicates with outlet port 98 of manifold 52 and is attached thereto by means of clamp 106.

The backflow valve assembly 56 is contained within a T-shaped member 108. One arm of the T-shaped member 108 adjacent the manifold outlet port 98 is formed with a valve seat 110. The valve seat 110 acts in conjunction with valve disc 112 and O-ring 114 found on the end of valve stem 116.

The valve stem 116 fills the remaining arm of the T-shaped section 108 and extends into an externally threaded nipple 118. One end of the nipple 118 is secured to the T-shaped member 108 by means of a clamp 120. An internally threaded cap 122 is threaded over the nipple 118.

Within the nipple 118 and cap 122 is a compression spring 124 which is held against the interior of the cap 122 by surrounding a projection 126 of the cap 122. The other end of the compression spring 124 is in contact with a washer 128. The washer 128 and the compression spring 124 surround a projection 130 at the end of the valve stem 116.

At the point where the T-shaped member 108 and the nipple 118 are joined together, the valve stem 116 passes through a flanged disc 132 surrounded by a gasket 134.

The body of the T-shaped member 108 is attached to a tubing connector 136 and held in place by means of a clamp 138.

The backflow valve assembly 56 operates by sensing a pre-established pressure within the main flow channel 90 of the manifold 52 and opens in response thereto. This allows a portion of the liquid flowing through outlet 98 to return to the tank 40 through tubing 60.

The actual pressure which is required to open the backflow valve assembly 56 is controlled by means of the cap 122. When the pump 50 is in service and positive pressure has been established throughout the lines, tightening down of the cap 122 over nipple 118 increases the minimal amount of pressure as shown in the pressure gauge 102 which will cause the valve stem 116 to lift against the compression spring 124. Conversely, loosening of the cap 122 over the nipple 118 will decrease the minimum amount of pressure as shown on pressure gauge 102 which will cause valve stem 116 to open, allowing return of liquids to the mixing tank 40.

In this manner, the internal pressure exerted on the tubing throughout the filtering system can be controlled within pre-established limits. This assures not only longevity of the tubing, but also eliminates the possibility of product loss which might occur if excessively high pressures were allowed to exist within the filtering apparatus during the filtering and filling process.

As further shown in FIGS. 4 and 5, the manifold assembly 52 is supported on a base 140 having stanchions 142. The stanchions 142 have attached clamps 144 which surround and hold the manifold main flow channel 90 in conjunction with rubber pillow blocks 146.

Thus, removal of the clamps 144 and pillow blocks 146 permits removal of the manifold 52 from its support base 140. Further removal of clamps 96, 88 and 138 disconnects all tubing from manifold 52. Complete disassembly of all parts is then effected by removal of clamps 104, 106 and 120, as well as cap 122. The separate parts can then be sterilized by steam sterilization or other sterilization methods.

It is preferred that the manifold and backflow valve assembly, pressure gauge, mixing tank and mixer, as well as all clamps, be composed of 316 stainless steel to permit their sterilization by autoclaving or other sterilization methods to prevent the growth of pathogenic organisms therein and thereon. The tubing can also be sterilized and the filters are obtained in a sterile condition. The pump does not actually contact the product and so does not require sterilization. However, the surfaces should be treated with an antibacterial agent on a regular basis.

The preferred filters for use in this invention are capsule filters 62 and 63 as shown in FIG. 6. As shown, fluid entering the capsule filter 62, preferably a 2 sq. ft. 0.2 micron nominal prefilter, from the outlet of the manifold 52 through tubing 64, not shown in FIG. 6, circulates through the filter. The path of filtration proceeds from just inside the exterior walls 146 through the filtration material 148 into a central passage 150 where it exits through an integrally formed tubing connection 152. The same path of filtration is followed in filter 63, preferably a 1 sq. ft. 0.2 micron absolute filter, which is directly downstream from filter 62.

The path of the fluid issuing from the filter 63 is to tubing 66 which bifurcates at a T-member 154 whereby tubing is attached by means of clamps 156, 158 and 160. Tubing 162 which is connected at one end to T-member 154 is attached at its opposite end to Y-shaped member 164 by means of clamp 168. Each of the legs of Y-member 164 is connected to a separate fill line 68 and secured thereto by means of clamps 170 respectively. Each fill line 68 is further provided with a pair of double clamps 177 and 179.

The sterile container or fill bag 70 for the liquid pharmaceutical products is shown in FIG. 7. The bag 70 is provided with an aperture 178 for hanging of the bag during the infusion process. In addition, there are two transfer ports 180 and 182 and a fill port 184. The fill port 184 has an integrally connected tube 185 which terminates in a spike not shown, attached to a shoulder portion 186. The shoulder portion 186 provides a means for grasping the spike. As shown in FIG. 6, the spike is covered by means of a protective plastic sleeve 188 which maintains sterility during the handling thereof. A clamp 190 permits separation of the spike from the fill line 68 without loss of product.

The fill bag or container 70 is preferably comprised of a clear plastic material such as polyvinylchloride sealed along its edges in a fluid tight relationship. The preferred type of bag is that called a transfer bag which is available commercially in a sterile, sealed condition.

Clarity is advantageous as color change in TPN solutions indicate deterioration thereof.

The transfer ports 180 and 182 remain sealed and capped prior to their use in the infusion process. They are utilized to add additional infusion liquids such as vitamins, fats, antibiotics and the like.

The material from which the tubing is composed is preferably also a clear plastic material which is capable of being sterilized and further is resistant to corrosives, solvents and temperature extremes. Excellent results have been obtained, using Tygon, Tygon food, silicone, and Viton (a trademark of E. J. Dupont de Nemours Co.) tubing having an inner diameter of approximately ⅜ inch and an outer diameter of approximately ⅝ inch.

All the tubing connections are made fluid tight by means of clamps and tubing connectors which are preferably made either of plastic or stainless steel which is capable of being sterilized by standard methods.

For best results, it has been found that keeping the internal tubing pressure below about 20 psi, significantly extends the tubing life.

The double clamping of the fill lines provides additional surety that if one fails during the fill process, there is another backup clamp.

PROCESS OF THE INVENTION

The process of the invention is illustrated schematically in the flow diagram of FIG. 3. The first step of the process is providing an aseptically clean room or enclosure which is substantially free of pathogenic organisms.

The mixing tank 40 and batch materials are located in a clean room or enclosure 43 which is separate from the clean room or enclosure 47 which houses the filtering and filling apparatus. This allows the compounding process to be done in a separate room from the filtering and filling processes.

In order to provide aseptic conditions, the equipment surfaces as well as floor, walls and ceiling are rendered aseptically clean by means of washing with an antibacterial agent, such as a water and chlorine bleach solution.

Delivering positive pressure air flow to each enclosure or clean room 43 and 47 as described for the apparatus, which air has been filtered through a high efficiency particulate air filter 26 prevents contamination by air carried dust particles. Preferably, this air is directed in a unidirectional substantially lateral flow pattern generally diagonally across the room or enclosure. Preferably, also, at least a portion of the air is refiltered and recirculated within the enclosure, and together with prefiltered makeup air maintains positive air pressure throughout the room. This prevents the entry of air from outside the enclosure and enables the use of rigid or flexible walls as desired. In fact, the maintenance of positive air pressure makes possible the use of overlapping strips of plastic in the entry areas without loss of air purity.

Preferably, technical personnel involved in the compounding of the liquid pharmaceutical products maintain themselves in as sterile a condition as possible. This is accomplished by first putting on surgical scrubs in a clean lab room 194. Surgical scrubs can be used in the mixing enclosure 43.

Before the filtering and filling process is begun, the technical personnel go to a change room 192 where a sterile suit is put on. Prior to entering the change room, the technical personnel put on a hair net, then scrub their hands with a germicidal soap and blot dry. Upon entering the change room 192, the surgical scrubs are removed and a sterile hooded suit is put on. A face mask is placed over the face and the hood of the suit is pulled up to cover the hair. Disposable sterile booties are put on and after entering the clean room for filtering and filling, sterile gloves are placed over the hands. Special care is taken not to allow the sterile suit to touch the floor.

The purpose of these elaborate preparations is to minimize the possibility of introducing pathogenic organisms into the clean room or enclosure.

As noted in the foregoing description, it is important that the mixing or compounding of the pharmaceutical liquids takes place in a clean room or enclosure 43 which is separate from the clean room or enclosure 47 where filtration and filling take place.

Within the compounding enclosure 43 provided with the highly purified air flow, batch materials, together with Water for Injection, U.S.P., are added to a mixing tank 40.

The manner of addition, as well as the various ingredients will be subsequently discussed in greater detail.

The prescription amounts of materials are carefully weighed and measured and then added in the prescribed order to the tank 40 with mixing. Mixing is continued to produce a homogeneous mixture. When this state is achieved, filtering of the product is begun in a separate clean room or enclosure 47 which communicates with the tank 40 by means of tubing 60 which passes preferably through a common wall.

A peristaltic pump 50 is started for pumping the mixture through a manifold 52 where a portion of the product is returned to the mixing tank 40 whenever the pressure within the manifold 52 reaches a minimum preestablished pressure.

From the manifold 52, the product is delivered to a high efficiency filter for liquids, preferably in the form of one or more capsule filters 62 and 63 as shown in the apparatus of FIG. 1, utilizing a polyester type of filtering material which is capable of excluding pathogenic organisms. The first filter 62 is preferably a 2 sq. ft. 0.2 micron nominal prefilter. The second filter 63 is preferably a 1 sq. ft. 0.2 micron absolute filter.

The product issuing from the filter 63 is directed to a fill bag 70 which according to a preferred embodiment, is filled on a scale 72 to permit the accurate measurement of the contents thereof. When each of the bags 70 has been filled, it is hermetically sealed, preferably double sealed, by means of a sealing device 78.

When the entire batch has been transferred to bags 70 and sealed, the filled bags are stored under refrigeration, preferably at 4 degrees C., prior to use by the patient.

By following the above described process steps, parenteral solutions can be produced from already prepared heat sterilized dextrose and heat sterilized amino acid solutions. Alternatively, a novel process is provided whereby the bulk powders of the dextrose, amino acid crystal materials, and bulk powders of electrolytes, can be combined. This new process as mentioned previously is all done at ambient temperatures without recourse to heat sterilization. The resulting products are moreover capable of a storage under refrigeration for up to thirty days or more. Moreover, such products are characterized by uniformity of composition. These characteristics enable the use of the parenteral prescription liquid to be administered in the home.

The actual compounding of the parenteral solutions within the claimed process from bulk amino acid and dextrose powders include first providing an individual patient prescription for a specific parenteral solution. The required ingredients which are required by the prescription are assembled in the clean mixing room enclosure, and the final volume of the solution is determined. Preferably, at least half of the volume of Water for Injection U.S.P. or other liquid is first added to the mixing tank. The mixer is started and the prescribed amount of amino acid powder is added slowly while continuing to mix until the amino acid powder is completely in solution.

Next, the prescribed amount of dextrose powder is slowly added with mixing, until the dextrose powder is completely in solution.

In compounding the parenteral solutions by this method it is important to add the amino acid powders to the water and be sure of dissolution before adding the dextrose powder.

At this point the pH of the mixture is adjusted according to the prescription by the addition of allowable acids. Typically, the pH of the prescription is adjusted by the addition of glacial acetic and/or phosphoric acid. Mixing is continued throughout this process.

The remaining prescription amounts of electrolytes and other minerals are then added. The exact order of addition of the electrolytes and trace minerals is not important, except for the Ca and Mg compounds. They should be added after all the other ingredients are present with the Mg compound being the last addition before the final amount of liquid. This process of mixing avoids the precipitation of salts and unwanted reactions between ingredients.

Typical minerals and electrolytes include but are not limited to $KH_2PO_4$ or $NaH_2PO_4$, KCl or KOAc, NaCl/NaOAc, $CrCl_2$, $CuCl_2$ or $CuSO_4$, $ZnCl_2$ or $ZnSO_4$, $MnCL_2$, a $CaCl_2$ or Ca Gluconate and $MgSO_4$.

The advantages of producing parenteral solutions from bulk amino acid and dextrose crystalline powders include versatility for individualized amino acid profiles, convenience, and decreased cost. Heretofore, presterilized amino acid solutions have been used which have been prepared according to standard specifications. According to this process, each amino acid can be added in the required amount, which is especially important in some disease states and for some patients as for example the pediatric patient. All of this is possible without having to resort to heat sterilization as the process of the invention permits the aseptic preparation under ambient temperature conditions.

Most preferably, approximately 75% of the volume of Water for Injection, U.S.P. required for the prescription is added prior to the addition of the amino acid powder. Also, it is preferred that approximately five minutes of mixing follow the addition of each ingredient. Longer periods of mixing could be required under some circumstances. The mixing should be continued throughout the compounding process with each ingredient being added only after inspection of the mixture shows the powder to be in solution.

When all the required ingredients have been added to the mixing tank and are in solution, the remaining volume of Water for Injection U.S.P. is added to provide the desired final volume.

When it is desired to prepare parenteral nutrition products using heat sterilized amino acid solutions and heat sterilized dextrose solutions substantially the same procedure is followed. That is, Water for Injection U.S.P. is added to the mixing tank, followed first by the addition of the heat sterilized amino acid solution. When this has been thoroughly mixed, the heat sterilized dextrose solution is then added to the tank, with thorough mixing. This is followed by pH adjustment and the addition of the remaining ingredients following the same steps described as for the compounding using the respective amino acid powders and dextrose powders.

A typical TPN prescription solution for an adult is given below.

TYPICAL TPN PRESCRIPTION SOLUTION FOR AN ADULT 500 ml 50% dextrose in water
500 ml 8.5% crystalline amino acids in water
15–30 mEq potassium acid phosphate (15–45 mM phosphorus)
20–30 mEq potassium chloride
40–180 mEq sodium chloride
3–5 mg zinc sulfate
2 mg copper sulfate
4.5–15 mEq calcium gluconate 10%
8–24 mEq magnesium sulfate To the above solution can be added at the time of infusion:

10 ml. multivitamin infusion typically containing:

| Vitamin A | 3,300 units |
|---|---|
| Vitamin D | 200 units |
| Vitamin E | 10 units |
| Vitamin $B_1$ | 3.0 mg. |
| Vitamin $B_2$ | 3.6 mg. |
| Niacin | 40 mg. |
| Pantothenic acid | 15 mg. |
| Vitamim $B_6$ | 4 mg. |
| Vitamin C | 100 mg. |
| Folic Acid | 400 mg. |
| Vitamin $B_{12}$ | 5 mg. |
| Biotin | 60 mg. |

Twice weekly there can be added at the time of infusion:

10–15 mg. Vitamin K.

A typical TPN solution for a pediatric patient is given below:

TYPICAL TPN SOLUTION FOR A PEDIATRIC PATIENT 500 ml. 40% dextrose in water
300 ml. 8.5% crystalline amino acids in water
30–40 mEq. potassium acid phosphate
25–30 mEq. sodium chloride
2 mg. zinc sulfate
0.5 mg. copper sulfate
25–35 mEq. calcium gluconate
12–15 mEq. magnesium sulfate To the above solution there can be added at the time of infusion:

2 ml. multiple vitamin infusion
0.5 mg. folic acid
1.0 mg. vitamin K
1 µg. Vitamin $B_2$
1 ml. Berocca-C (100 µg biotin)

The amino acid solution used in the above typical TPN solutions can vary according to its amino acid profile just as the nutritional prescription can vary as well. In Table I below, typical amino acid profile solutions are given.

TABLE I
AMINO ACID SOLUTIONS
(8.5% in Water in g/ml)

| AMINO ACID | 1 | 2 | 3 | 4 |
|---|---|---|---|---|
| L-isoleucine | 0.62 | 0.59 | 0.90 | 0.483 |
| L-leucine | 0.81 | 0.77 | 1.10 | 0.590 |
| L-lysine | 0.62 | 0.62 | 0.61 | 0.328 |
| L-methionine | 0.34 | 0.45 | 0.10 | 0.053 |
| L phenylalanine | 0.38 | 0.48 | 0.10 | 0.052 |
| L-threonine | 0.46 | 0.34 | 0.45 | 0.241 |
| L-valine | 0.68 | 0.56 | 0.84 | 0.450 |
| L-tryptphan | 0.15 | 0.13 | 0.07 | 0.035 |
| L-alanine | 1.10 | 0.60 | 0.77 | 0.410 |
| L-arginine | 0.85 | 0.81 | 0.60 | 0.322 |
| L-histidine | 0.26 | 0.24 | 0.24 | 0.128 |
| L-proline | 0.75 | 0.95 | 0.80 | 0.429 |
| L-serine | 0.37 | 0.50 | 0.50 | 0.268 |
| L-tyrosine | 0.044 | — | — | — |
| Glysine | 1.10 | 1.19 | 0.90 | 0.483 |
| L-cysteine HCl—H2O | — | 0:02 | 0.02 | — |

The above listed amino acid solutions, as well as the typical TPN solutions are given for the purposes of illustration and are not intended to constitute any limitation of the invention. The invention process is primarily directed to the aseptic process of making such prescription solutions, as well as other intravenous infusion solutions. The products made by the invention process steps are also novel though not limited to the individual ingredients.

For example, the aseptic process involving the compounding, filtering and filling process is applicable to total parenteral solutions, as well as to the preparation of other types of intravenous infusions. Examples of the latter might include the production of sterile amino acid solutions, the preparation of antibiotic solutions, the preparation of chemotherapy solutions, the preparation of dextrose solutions, or virtually any other pharmaceutical solution which contains ingredients which will pass through the high efficiency filter used in the invention process.

Furthermore, the production of dextrose and amino acid containing nutritional solutions for infusion which are produced from the bulk crystalline ingredients and water, are also unique.

The following examples are given for purpose of illustrating the invention and are not intended to constitute a limitation thereof. References to the apparatus, compounding room and filling and filtering room are as described in the drawings.

EXAMPLE 1

A pharmacist technician upon arrival at the pharmaceutical facility removed his street clothes and put on surgical scrubs.

Upon receipt of a pharmaceutical prescription for a specific batch of TPN for a patient, the pharmacist technician ordered the specific materials required and had them delivered to the compounding room. The specific prescription is given below.

In a special room set aside near the compounding room, the pharmacist technician removed his surgical scrubs and put on a clean set of surgical scrubs. A fresh hair cover, mask, and shoe covers were also put on.

The pharmacist technician then entered the compounding room and washed his hands with an antibacterial soap and dried them. Inside the compounding room, the pharmacist technician put on sterile latex gloves.

The walls, floor, ceiling and mixing equipment and wash surfaces within the compounding room had been previously disinfected by washing with an antibacterial solution. In addition, work surfaces and equipment, as well as parts of the walls and ceiling had been tested for a bacterial growth count.

The filtering and filling room had also been treated in the same manner in order to render the room substantially free of pathogenic organisms.

Positive pressure air was delivered to the compounding room and to the filtering and filling room. Prior to entry into each of the rooms it was filtered through a high efficiency particulate air filter which provided an efficiency of at least 99.99% rejection of 0.3 micron sized particles. The arrangement of the room was substantially as described in FIGS. 1 and 2 of the drawings. The air was made to travel diagonally across each room to an opposite return grill where prefiltered makeup air was added for further filtration and recirculation through each room. In this manner the air in each room was renewed each 15 seconds.

The mixing procedure which took place in the compounding room involved adding approximately 75% of the final volume of the TPN solution (about 18 l.) in the form of Water for Injection U.S.P. to a mixing tank equipped with a mixer. The mixer was started and continued throughout the mixing process.

Prior to the opening of each container, the top was washed off with an antibacterial agent. The prescribed amount of each amino acid powder was added to the mixing tank and mixed for approximately five minutes. The following amino acids were added after weighing in the order listed:

| AMINO ACID PROFILE PER BATCH | |
|---|---|
| L-Alanine | 48.53 gm. |
| L-Arginine | 65.51 gm. |
| L-Cysteine HCl | 1.62 gm. |
| L-Glycine | 96.25 gm. |
| L-Histidine | 19.41 gm. |
| L-Isoleucine | 47.72 gm. |
| L-Leucine | 62.28 gm. |
| L-Lysine: OAC | 70.37 gm. |
| L-Methionine | 36.40 gm. |
| L-Phenylalanine | 38.82 gm. |
| L-Proline | 76.84 gm. |
| L-Serine | 40.44 gm. |
| L-Threonine | 27.50 gm. |
| L-Tryptophan | 10.51 gm. |
| L-Tyrosine | — |
| L-Valine | 45.29 gm. |
| | 693.49 gm. |

When all of the amino acid powder appeared to be completely in solution, 5.68 kg. of dextrose powder was added to the mixing tank and allowed to mix for approximately five minutes. When inspection showed the powder to be completely in solution, the pH was adjusted with 11 ml. of 85% phosphoric acid and 18.60 ml. of 99.4% glacial acetic acid.

When this had been completed, 182 ml. of a 4/1 aqueous solution of sodium chloride was added followed by 103 ml. of a 3/1 aqueous solution of sodium phosphate. When thoroughly mixed, 193 ml. of a 2/1 aqueous solution of potassium chloride was added. This was followed by the addition of 35 ml. of a 4/1 aqueous solution of potassium acetate. When the mixing had been continued to produce dissolution of the additives, 29 ml. of a multiple electrolyte solution was added, followed by the addition of 10 ml. of a 5/1 aqueous solution of zinc injection.

When thoroughly mixed, 533 ml. of a 10% aqueous solution of calcium gluconate was added with mixing. When this had been thoroughly mixed in, the final ingredient added was 33 ml. of a 50% aqueous solution of magnesium sulfate. The remaining amount of Water for Injection U.S.P. which was required to produce a final volume of 25 liters was then added to the mixing tank.

Upon completion of the above produced solution, the pharmacist technician exited from the compounding room. In preparation for the sterile aseptic filtering and filling process, he scrubbed his hands with a germicidal soap, rinsed them well and, using a paper towel, blotted them dry. A fresh hair net was then placed on his head, followed by his entering a change room adjacent the filtering and filling room. There he removed his surgical scrubs and put on a sterile, one piece suit with a hood.

Care was taken in putting on the sterile suit so that the suit did not touch the floor. A sterile face mask was then put on, as well as disposable shoe covers or booties.

At this point, the pharmacist technician entered the filtering and filling room and put on sterile gloves. The outside of the gloves was then rinsed with eighty percent isopropyl alcohol.

An empty fill bag was placed on the scale to set the Tare weight. The pump was started long enough to purge any air from the system.

All but one of the fill lines was clamped off and one of the lines was attached to the fill bag on the scale. The pump was started and the back flow valve was adjusted so that the pressure gauge read no more than twenty psi. As each fill bag was filled, it was aseptically disconnected from the fill line and replaced by another fill bag. The tubing of each fill bag was sealed with a heat sealer. When all of the batch had been pumped into the fill bags, they were then stored under refrigeration at four degrees centigrade. A total of 15 fill bags were filled, each bag having a volume of 1350 ml. and a specific gravity of 1.09.

EXAMPLE 2

Substantially the procedure of Example 1 is followed with the exception that presterilized amino acid solutions and presterilized dextrose solutions are used in place of the bulk amino acid powders and dextrose powders.

EXAMPLE 3

Each of the amino acid solutions described in Table I is prepared from the bulk amino acid crystal powders substantially following the procedure of Example 1.

EXAMPLE 4

Substantially the procedure of Example 1 is followed to produce a sterile dextrose water solution according to a prescription using bulk dextrose powder. The prescribed amount of dextrose powder is added to sterile water in the mixing tank with stirring. When the powder is in solution, the resulting solution is filtered and pumped into fill bags according to the process of Example 1.

Various modifications of the invention are contemplated and can be resorted to without departing from the spirit and scope of the invention as defined by the following claims.

We claim:

1. Apparatus for the aseptic compounding at ambient temperatures of liquid pharmaceutical products for usage by a patient comprising:
    mixing means having at least one inlet means and at least one outlet means therefrom wherein ingredients for liquid pharmaceutical products can be implaced and mixed;
    first conduit means from said outlet means of said mixing means;
    filter means for filtering liquids;
    flow means for providing flow through said first conduit means to said filter means;
    container means;
    second conduit means from said filter means to said container means into which said liquid pharmaceutical products are to be delivered;
    one or more enclosures having prefiltered air free of pathogenic organisms delivered to it through a filtration unit;
    means for recirculating at least a portion of said prefiltered air within each enclosure after it has been filtered again to remove pathogenic organisms; and,
    said mixing means, first and second conduit means, filter means, flow means and container means contained within one or more of said enclosures.

2. The apparatus as claimed in claim 1 further comprising:
    meter means for controlling the rate of flow into said container means; and,
    sealing means for sealing said container means.

3. The apparatus as claimed in claim 1 further comprising:
    third conduit means from one of said outlet means of said mixing means;
    diverting means connected to at least one of said inlet means of said mixing means.

4. The apparatus as claimed in claim 1 wherein:
    said diverting means comprises a manifold having a return means to said mixing means.

5. The apparatus of claim 1 wherein said flow means is comprised of:
    pump means in communication with one of said outlet means of said mixing means for pumping liquid pharmaceutical products through said first conduit means to and through said filter means and then to said container means.

6. The apparatus of claim 1 wherein:
    said mixing means is in a separate enclosure.

7. A liquid filtering apparatus for the aseptic preparation of liquid pharmaceutical products comprising:
    a mixing tank equipped with a stirring means;
    at least one outlet port in said tank;
    at least one inlet port in said tank;
    a manifold having a main flow channel;
    means for detecting pressure within said main channel;
    at least one diversion channel connected to said main flow channel;
    valve means connected to said diversion channel which opens under pre-established pressure;
    return means from said valve means for returning flow to said mixing tank through said diversion channel upon sensing of said pre-established pressure;
    first tubing means communicating with said outlet of said tank and said main flow channel of said manifold;

second tubing means communicating with said mixing tank inlet port and said diversion channel of said manifold;

at least one filter for liquids having pores small enough to preclude passage of pathogenic organisms;

at least one fill bag for said liquid pharmaceutical products;

third tubing means communicating with said main flow channel of said manifold and said filter;

fourth tubing means communicating with said filter and said fill bag;

pump means for establishing and maintaining positive pressure flow from said mixing tank through said manifold, filter and tubing means to said fill bag; and, metering means between said filter and said fill bag for controlling the rate of flow into said fill bag.

8. The apparatus as claimed in claim 7 wherein:

said pressure means within said main channel is comprised of a pressure gauge; and wherein, said valve means comprises a back pressure valve within said diversion channel.

9. The apparatus of claimed in claim 7 wherein:

said pump means is comprised of a peristaltic pump.

10. The apparatus as claimed in claim 7 further comprising:

tube sealing means to hermetically seal the tube communicating with said fill bag.

11. The apparatus of claim 7 wherein:

said tubing means communicating between said filter and said fill bag is bifurcated at least one time to produce at least two fill lines; and wherein, said metering means comprises at least one clamping means for each of said fill lines.

12. The apparatus as claimed in claim 7 wherein:

said mixing tank, manifold and valve means are comprised of stainless steel and wherein said filter is a sterile capsule filter, and wherein said fill bag is a blood bag.

13. Apparatus for controlling and maintaining the pressure of liquids flowing therethrough which is useful in the compounding of liquid pharmaceutical products such as parenteral, enteral, and other nutritional products comprising:

a main flow channel;

means for detecting pressure within said main channel;

at least one diversion channel connected to said main flow channel;

valve means connected to said diversion channel which opens under pre-established pressure; and, means from said valve means for returning flow to an original source from which flow is initially established through said main flow channel when such pre-established pressure is sensed within said main flow channel.

14. The apparatus of claim 13 further comprising:

a manifold containing said main flow channel including a main inlet port and a main outlet port with two secondary outlet ports;

a pressure gauge within said secondary outlet port adjacent to said inlet port of said main channel;

a back pressure flow valve within said secondary outlet port adjacent said main outlet port, said back pressure valve comprising a T-shaped member having a pair of arms attached to a body member wherein one arm is attached to said manifold outlet port adjacent said inlet port, the body member of said T-shaped member comprising a diversion channel for returning flow to an original source from which flow is established initially through said main flow channel;

a movable piston inserted within the remaining open arm end of said T-shaped member;

a compression spring in contact with said piston arm;

means for adjustably exerting pressure against said compression spring in contact with said piston arm and thus controlling the minimum amount of internal pressure within said manifold which will cause the opening of said valve to said diversion channel, said pressure gauge permitting the measurement of the actual pressure within said main flow channel needed to open said back flow valve.

15. A process for preparing aseptic pharmaceutical liquids at ambient temperatures for medical usage comprising:

providing one or more enclosures substantially free of pathogenic organisms;

delivering air to each said enclosure which has been filtered to remove pathogenic organisms;

recirculating air within said enclosures and filtering it to remove pathogenic organisms for delivery back to said enclosures;

providing a mixing tank within one of said enclosures;

providing prescription amounts of dry and liquid ingredients sufficient to prepare liquid pharmaceutical products;

placing within said mixing tank prescription amounts of dry and liquid ingredients for the preparation of liquid pharmaceutical solution;

mixing said dry and liquid ingredients together to form a solution;

providing filtering and filling apparatus within one of said enclosures;

conducting said mixture from said mixing tank to said filtering and filling apparatus;

filtering said mixture through one or more high efficiency liquid filters which excludes pathogenic organisms; and, implacing said mixture into at least one sterile container.

16. A process as claimed in claim 15 further comprising:

providing said air as a positive pressure air flow which has been filtered to remove pathogenic organisms through a high efficiency particulate air filter in a unidirectional substantially lateral flow pattern diagonally across the enclosure;

filtering said liquid pharmaceutical product through one or more high efficiency capsule filters which exclude all particles smaller than about 0.22 microns; and, providing an enclosure for said mixing tank which is separate from any enclosure for said filtering and filling apparatus.

17. The process as claimed in claim 15 further comprising:

delivering said liquid pharmaceutical products from said mixing tank under pressure to said filter;

monitoring said pressure; and, diverting at least a portion of said liquid pharmaceutical products from said filter back to said mixing tank when pressure is established above a pre-established limit.

18. A process as claimed in claim 15 wherein:

said liquid pharmaceutical product is a parenteral solution.

19. A process as claimed in claim 18 further comprising:
compounding said parenteral solutions from dextrose solutions and aminoacid solutions each of which has been presterilized prior to admixture.

20. A process as claimed in claim 18 further comprising:
compounding said parenteral solutions from bulk crystalline aminoacid powders and bulk crystalline dextrose powders.

21. The parenteral solutions produced according to the process of claim 19.

22. The parenteral solutions produced according to the process of claim 20.

23. A process as claimed in claim 15 further comprising:
selecting said liquid pharmaceutical products from the group consisting of parenteral solutions, dextrose solutions, aminoacid solutions, electrolyte solutions, vitamin solutions, antibiotic solutions, antifungal solutions, and chemotherapy solutions.

24. A process for making aseptic liquid pharmaceutical products at ambient temperatures for parenteral feeding of a patient comprising:
providing bulk crystalline materials;
mixing said bulk crystalline materials with a liquid to produce a solution;
causing said liquid solution to flow through one or more high efficiency filtration filters capable of excluding pathogenic organisms from flow therethrough; and,
delivering the filtered liquid mixture to containers for direct use with respect to the provision of such feeding mixtures to a patient.

25. A process as claimed in claim 21 wherein the process steps of compounding the parenteral solutions containing aminoacid and dextrose powders further comprises:
providing a prescription of said parenteral solutions;
providing the ingredients required for said prescription;
determining the final volume of the parenteral solution to be produced;
adding at least half of the volume of Water for Injection, U.S.P. water into a mixing tank;
starting the mixer in the mixing tank;
adding the prescribed amount of aminoacid powder slowly with the mixer in operation;
mixing the resulting mixture until the aminoacid powder is completely in solution;
adding slowly with mixing the prescribed amount of dextrose powder;
mixing until the dextrose powder is completely in solution;
adjusting the pH of the mixture according to the prescription;
adding the remaining prescription amounts of the electrolytes and minerals with the exception of magnesium and calcium;
mixing thoroughly;
adding the calcium-containing compound;
mixing thoroughly;
adding the magnesium compound;
mixing thoroughly; and,
adding with mixing the remaining volume of Water for Injection U.S.P. to provide the desired final volume.

26. The parenteral solutions produced according to the process of claim 24.

27. The liquid parenteral solutions containing prescription amounts of amnioacids, dextrose and electrolytes produced according to the process of claim 25.

28. A process as claimed in claim 24 further comprising:
delivering said liquid pharmaceutical products under pressure to a filter;
monitoring said pressure; and,
diverting at least a portion of said liquid pharmaceutical products from said filter back to said original mixing source when pressure is established above a pre-established limit.

* * * * *